(12) United States Patent
Ventura et al.

(10) Patent No.: US 12,303,638 B2
(45) Date of Patent: May 20, 2025

(54) LARGE DOSE DISPOSABLE INHALER AND METHOD OF SIMPLE FILLING

(71) Applicant: Hovione Technology Ltd, County Cork (IE)

(72) Inventors: João Ventura, Lisbon (PT); Peter Villax, Lisbon (PT); Agostinho Carvalho, Leiria (PT); Daniel Caramelo, Lisbon (PT); Sónia Josué, Caldas Da Rainha (PT)

(73) Assignee: HOVIONE TECHNOLOGY LTD, County Cork (IE)

( * ) Notice: Subject to any disclaimer, the term of this patent is extended or adjusted under 35 U.S.C. 154(b) by 875 days.

(21) Appl. No.: 17/311,164

(22) PCT Filed: Nov. 20, 2019

(86) PCT No.: PCT/EP2019/081993
§ 371 (c)(1),
(2) Date: Jun. 4, 2021

(87) PCT Pub. No.: WO2020/114783
PCT Pub. Date: Jun. 11, 2020

(65) Prior Publication Data
US 2022/0023553 A1    Jan. 27, 2022

(30) Foreign Application Priority Data

Dec. 4, 2018   (PT) .......................................... 115189

(51) Int. Cl.
*A61M 15/00*   (2006.01)
*A61M 15/08*   (2006.01)

(52) U.S. Cl.
CPC .... *A61M 15/0086* (2013.01); *A61M 15/0021* (2014.02); *A61M 15/08* (2013.01); *A61M 2202/064* (2013.01); *A61M 2209/045* (2013.01)

(58) Field of Classification Search
CPC .......... A61M 15/0086; A61M 15/0021; A61M 15/08; A61M 2202/064; A61M 2209/045;
(Continued)

(56) References Cited

U.S. PATENT DOCUMENTS

| 4,860,740 A | * | 8/1989 | Kirk | .................. | A61M 15/0028 |
| | | | | | 128/203.15 |
| 2009/0178676 A1 | * | 7/2009 | Villax | ............... | A61M 15/0045 |
| | | | | | 128/203.15 |

FOREIGN PATENT DOCUMENTS

| CN | 101443066 A1 | 5/2009 |
| PT | 103481 A | 11/2007 |

(Continued)

*Primary Examiner* — Elliot S Ruddie
(74) *Attorney, Agent, or Firm* — 24IP Law Group USA, PLLC; Timothy R. DeWitt (57) ABSTRACT

A dry powder inhaler for pulmonary or nasal use, comprising at least an inhaler body (201) and a cartridge (203) with a plurality of powder compartments (205) each including one dose of a drug. The body (201) has an opening (204) shaped for receiving the cartridge (203) and the plastic body recess (215) and the detent (218) to allow a controlled advancement and turning movement of the cartridge (203) relative to the body (201) for sequentially delivering each of the plurality of unit doses filled into the cartridge compartments (205). The inhaler construction is suitable for filling the plurality of unit doses into the compartments (205) with the cartridge (203) assembled into the body (201). The invention affords a large dose inhaler of single-use and low cost that improves industrial filling and manufacturing cost for the delivery of high dosages of inhaled medicines.

8 Claims, 10 Drawing Sheets

(58) Field of Classification Search
CPC .......... A61M 15/0023; A61M 2206/16; A61M 15/005; A61M 15/0048
See application file for complete search history.

(56) References Cited

FOREIGN PATENT DOCUMENTS

| | | | |
|---|---|---|---|
| PT | 105065 | A | 4/2010 |
| PT | 108426 | A | 10/2016 |
| WO | 98/41265 | A1 | 9/1998 |
| WO | 2007/132217 | A1 | 11/2007 |
| WO | 2016/184393 | A1 | 11/2016 |

\* cited by examiner

LARGE DOSE DISPOSABLE INHALER AND METHOD OF SIMPLE FILLING

BACKGROUND OF THE INVENTION

Field of Invention

The present invention describes a novel disposable pulmonary or nasal inhaler of simple construction and operation, ease of industrial filling and low cost suitable for the delivery of very large doses of pharmaceutical compounds.

Inhalers used for the delivery of pharmaceutical compounds have become widespread, particularly powder-based inhalers which use the patient's inspiratory effort as source of energy for drug delivery, mainly for the treatment of chronic respiratory diseases such as asthma or the chronic obstructive pulmonary disease, but also for the treatment of acute conditions, such as to deliver anti-infectious drugs, rescue drugs in emergency respiratory situations and to deliver antibiotics and cancer locally to the diseased lung. In addition, the potential of the fast drug onset and lower total dose from pulmonary drug delivery by powder inhalers has also been explored for systemic drug delivery. An example of this systemic drug delivery is inhaled insulin which has been a widely known scientific and commercial breakthrough.

Presently, looking ahead to the drug development pipeline, there is growing interest in delivering very large doses of drugs from powder inhalers, a non-limiting example being in the range of 100 to 400 mg, as it is anticipated that the molecule types of the drugs used for the treatment of asthma, the chronic obstructive pulmonary disease and other respiratory conditions, shifts predominantly from highly potent, small molecules to large biopharmaceutical molecules, such as proteins, peptides, antibodies, oligonucleotides and even gene/cell/RNA based biologic compounds, which are all required to be delivered in large doses to the patients.

Moreover, these compounds (large biopharmaceutical molecules) are required to be formulated by sophisticated particle engineering technologies in carrier free, high drug load formulations and delivered very efficiently to minimize drug losses, as such biopharmaceutical molecules are extremely expensive, from multiple consecutive inhalations performed by the patient from a large powder volume filled into and made available by the inhaler, since that efficient delivery minimizes the "powdery mouth" effect, throat irritation and extensive drug losses in the upper airways.

From the above it is thus required a large dose powder inhaler, capable of delivering efficiently a drug dose in the range between 100 and 400 mg of carrier free formulations, conveniently to the patient from multiple consecutive inhalations. As such a large dose inhaler of single-use has not been presented yet, a major challenge presented to the developer is designing an inhaler that is of simple use and construction, easy to fill industrially with current, traditional powder filling technologies, and which can be manufactured in high volume at a low unit cost of goods.

Discussion of Prior Art

There is abundant prior art in the field of single-use disposable inhalers, but a very large disposable inhaler solving the above requirements has not been provided yet. The present application is particularly directed at the inventive improvement of the inhaler described in Portuguese patent applications numbers PT103481 and PT108426, both of which are assigned to Hovione.

Figures 1A, 1B:
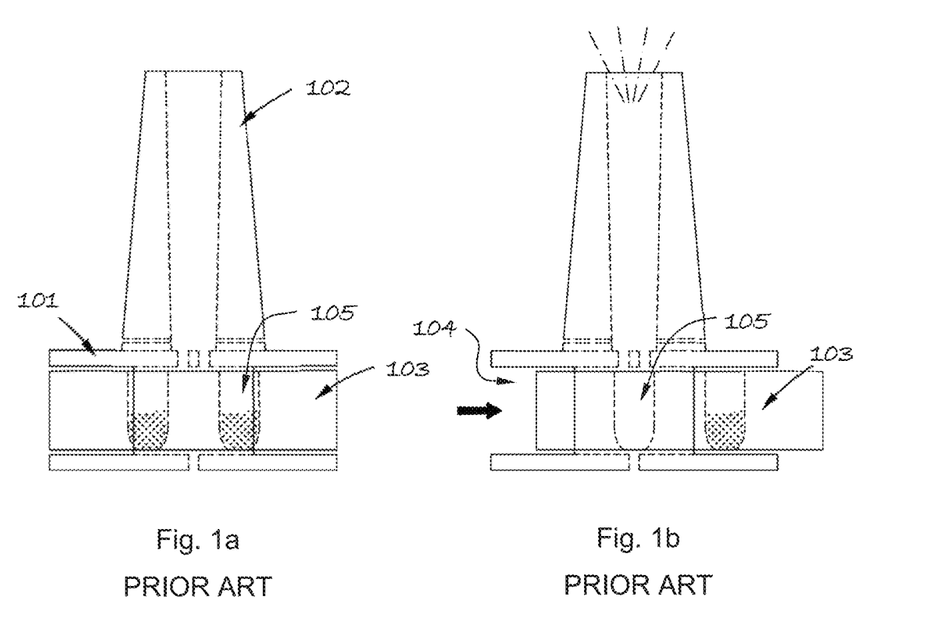
FIGS. 1a to 1d show prior art inhalers.
Figure 1C:
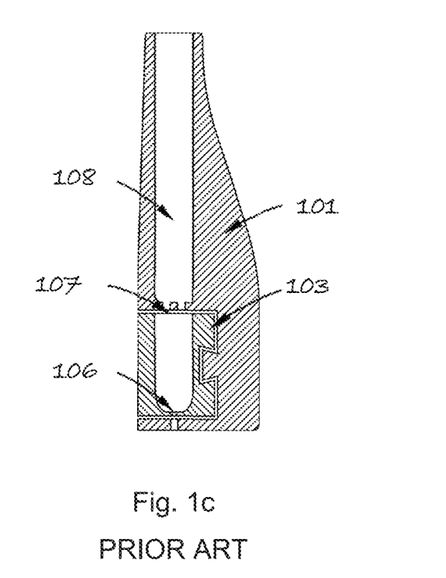

Previously, in PT103481, there was known a disposable inhaler comprising a body 101 including a mouthpiece 102 and a cartridge 103 mounted in an opening 104 provided in the body 101 and having at least one powder compartment 105. The powder compartment 105 had inlet holes 106 to admit air and outlet holes 107 to communicate with a body inhalation channel 108 provided in the body 101. Furthermore, the cartridge 103 was made slidable relative to the body 101 by the patient, between a first position detailed in FIG. 1a in which the compartment inlet holes 106 and the outlet holes 107 were isolated and sealed, and a second position, detailed in FIGS. 1b and 1c, in which the compartment inlet holes 106 and the outlet holes 107 were aligned with the body inhalation channel 108, thus allowing the flow of air to disperse and entrain the powder through the mouthpiece 102 and into the patient's mouth or nasal cavity and finally into the desired site of action. The construction disclosed in PT103481 allowed for a device with pre-filled unit doses of powder for patient convenience, disposable for reasons of safety and hygiene, simple for economic reasons and intuitive for ease of use by the patient. While this disposable inhaler is being successfully marketed, the maximum deliverable dose is in the region of 10-20 mg of powder.

Figure 1D:
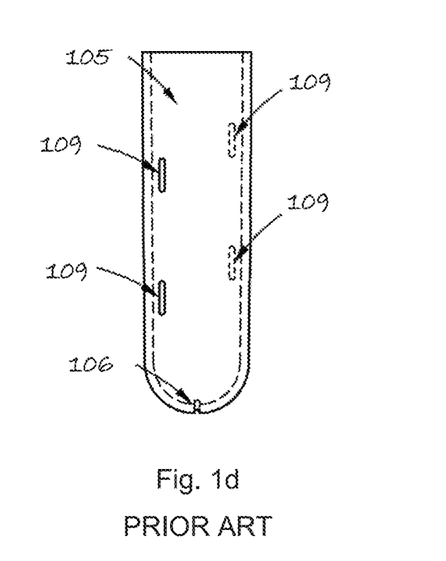

Previously, in PT108426, there was known an inventive improvement to the disposable inhaler disclosed in PT103481, and detailed in FIG. 1d, where additional air inlets 109 were placed into the cartridge compartment 105 in an inventive disposition that created novel, effective dispersive and aerosolization dynamics leading to operation with higher deliverable doses, in the region of 50 to 100 mg.

However, both the constructions of the disposable inhalers described in PT103481 and PT108426, require industrial scale filling of the disposable inhaler to be setup in an inhaler disassembled configuration, as the powder volume is required to be filled into the cartridge while this cartridge is dissembled in relation to the body of the disposable inhaler, and such cartridge is positioned in an specifically designed, industrial scale capable, automated mechanical apparatus that provides sealing of the cartridge compartment inlet during filling, and then immediate displacement of the filled cartridge and mechanical assembly into the body, into the position where the compartment holes are isolated and sealed, and these filling requirements have been found to lead to additional powder losses and manufacturing complexity and cost.

SUMMARY OF THE INVENTION

We have now invented a novel large dose inhaler of single-use comprising only two components that improves the constructions of the disposable inhalers as disclosed in the prior art patent applications PT103481 and PT108426 for the delivery of up to 400 mg of inhalation powders, while maintaining an inhaler that is simple and intuitive to use and that can be manufactured at a very low cost. Furthermore, we have invented a large dose single-use (disposable) inhaler of simple use, construction and low cost that is suitable for filling in an assembled inhaler configuration which maximizes ease of industrial filling with traditional powder filling machines, and minimizes both powder filling losses and manufacturing complexity and cost, and this a highly advantageous improvement to the constructions disclosed in PT103481 (Hovione) and PT108426 (Hovione)

which required filling to take place in a disassembled inhaler configuration, and this is novel.

The present invention comprises two plastic-injected components as known in the prior art patent applications PT103481 and PT108426: an inhaler body and a powder cartridge. The body and cartridge are locked together after assembly to form the integral and functional disposable inhaler.

As in disposable inhalers disclosed in the prior art Portuguese applications, PT103481 and PT108426, the inhaler body is provided with a mouthpiece or nosepiece, an opening shaped for receiving and holding in place a cartridge and an inhalation channel for providing fluid communication between the patient's mouth or nose when engaged with the mouthpiece or nosepiece and the assembled cartridge. One or more body side inlets are provided to admit air directly from the atmosphere to the inhalation channel. In addition, there is at least one body bottom opening, included in the bottom wall of the body opening shaped for receiving the cartridge, to allow the admission of air from the atmosphere into the cartridge powder compartment when the cartridge is moved into the inhalation position.

As in the prior art Portuguese applications PT103481 and PT108426, the cartridge includes at least one powder compartment, that is built or moulded into the cartridge, and which is tapered cylindrical or near-cylindrical shape with rounded extremities absent of sharp angles, such as spherical, oval and the like to minimize powder retention during and after inhalation. The cartridge comprises at least one powder compartment which is movable when mounted in the body opening. In addition, there is at least one compartment bottom inlet for admission of air that is of very small size, between 0.1 and 2 mm in width, and in one aspect 1 mm or less in width. The shape of the cartridge is tapered in the direction of the powder compartment to create a "funnel" that blocks the flow of powder under gravity and other forces. Furthermore, as known in PT103481 and PT108426, the powder compartment comprises also an outlet, normally of the same or similar diameter as the compartment itself, to allow normal filling and automated high-speed filling of the powder and to allow fluid communication with the body inhalation channel through the body bottom inhalation channel inlet when the cartridge is moved into the inhalation position.

However, the inhaler of the present application includes new features not found in the inhaler described in the prior art Portuguese patent applications PT 105065, or PT108426, or in the prior art, and these new features are now detailed.

In the inhaler of this document, the inhaler body further comprises top and bottom walls in the body opening. The top and bottom walls are shaped for receiving the cartridge and are of cylindrical or near-cylindrical shape, with round extremities absent of sharp edges, as well as comprising at least one rail, preferably located at the top body wall, to allow the cartridge of cylindrical or near-cylindrical shape to be pivoted or turned in relation to the body, from multiple initial positions of the cartridge, at which initial positions the cartridge compartment is sealed, into a final position where the cartridge compartment becomes aligned with the body inhalation channel and air inlets and outlets included in the compartment are available for air admission and in communication with the body inhalation channel.

Furthermore, the inhaler body of this document comprises a hinged or foldable lid of a snap type, included in the top, cylindrical shaped wall of the body opening shaped for receiving the cartridge, injection moulded in the same material and moulding step as the body itself. The said body top wall hinged lid is moveable or foldable from a first open position, at which first open position the cartridge is assembled into the body and the cartridge compartment bottom inlet is sealed by the body bottom wall of cylindrical shape, and which is suitable to allow easy, effective industrial scale powder filling into the sealed cartridge compartment, into a second closed position, at which second closed position the cartridge assembled into the body is sealed by the body bottom, the cylindrical shaped wall and the said closed top wall hinged lid of snap type.

The hinged or foldable lid of snap type, as described above, included in the top, cylindrical shaped wall of the body opening shaped for receiving the cartridge, in addition comprises at least one plastic recess shaped to be engageable with one or more plastic protrusions included in the cartridge, to provide the device for advancing and controlling the pivoting or turning motion of the cartridge in relation to the body and to limit its turning travel between multiple initial positions, at which each multiple initial positions each of the plurality of cartridge compartments is sealed, into a final position at which final position each of the plurality of cartridge compartments becomes aligned with the body inhalation channel and air inlets and outlets included in the compartment are available for air admission and in communication with the body inhalation channel, including a non-return device to provide a non-return interference between the cartridge and the body, once said cartridge advancement is conducted.

Moreover, in this inhaler, the bottom, cylindrical shaped wall of the body opening shaped for receiving the cartridge, comprises at least one plastic protrusion engageable with the corresponding bottom, cylindrical shaped wall of the cartridge, which provides a snap type assembly between the body and cartridge and a full mechanical locking between the same following assembly.

In this inhaler, the inhaler cartridge further comprises a cylindrical or near-cylindrical shape providing the space to accommodate a plurality of powder compartments, preferably four, eight or ten, suitable for filling, storing and delivering up to 400 mg of inhalation powders.

The inhaler cartridge further comprises top and bottom walls which are of cylindrical or near-cylindrical shape, with round extremities absent of sharp edges, and comprising at least one plastic protrusion for each of the plurality of powder compartment therein, preferably located at the top cartridge wall, engageable with the body cylindrical rail and with the top wall hinged lid plastic recess, to provide a device for advancing and controlling the pivoting or turning motion of the cartridge in relation to the body and limit its turning travel between multiple initial positions, at which multiple positions each of the plurality of cartridge compartments is sealed, into a final position, at which final position each of the plurality of cartridge compartments becomes aligned with the body inhalation channel and air inlets and outlets included in the compartment are available for air admission and in communication with the body inhalation channel, including a non-return device to provide a non-return interference between the cartridge and the body, once said cartridge advancement is conducted.

Additionally, the inhaler cartridge includes at least one cartridge hand grip or holder, preferably of cylindrical shape, or multiple hand grips spaced across the cartridge, included in the cartridge frontal wall opposing the body opening shaped for receiving the cartridge, engageable with the patient's fingers and providing the device for a comfortable, easy, low friction turning of the cartridge in relation to the body between multiple positions.

In another aspect of the inhaler of the present invention, the inventive inhaler components described above, instead of pivoting or turning about one another, can be constructed as to be operated in a straight line, linear motion, where the cartridge slides perpendicularly to the axis of the mouthpiece.

The inhaler body and the cartridge can be made by injection-moulding of any suitable material for pharmaceutical use such as polyethylene (PE), polypropylene (PP), polysulfone (PSU), acrylonitrile butadiene styrene (ABS), polymethylmetacrilate (PMMA), polycarbonate (PC), polypropilene oxide (PPO), polybutylene terephthalate (PBT) polyethylene terephthalate (PET), liquid crystal polymer (LCP), polyethyleneimine (PEI), polyphenylenesulphide (PPS). Material selection should be made to maximize compatibility with the powder to be contained and delivered, minimize retention during inhalation and degradation during storage and allow transparency if possible.

Following manufacturing, the cartridge is inserted into the body of the inhaler through the opening shaped for receiving it and the engagement of snap type between the body bottom wall protrusions and the bottom cartridge wall provides full assembly and mechanical locking between the body and the cartridge, while allowing a low friction free turning movement between the cartridge and the body for the filling process.

Following assembly, the plurality of inhaler cartridge powder compartments are available and ready to be filled by conventional powder filling equipment through the body lid of snap type described above, included in the top, cylindrical shaped wall of the body opening, which is in the opened position following injection moulding of the body, and thus allows a unit dose of inhalation powder to be dispensed into each of the plurality of powder compartments included in the cartridge, while this cartridge is turned sequentially, without mechanical constraints during the filling process.

Following filling of the cartridge, the body lid, included in the top, cylindrical shaped wall of the body opening, is moved or folded from the open position into the closed position and snapped into and against the said top wall of the body opening, providing close mechanical contact and sealing interference with each compartment outlet included in plurality of cartridge powder compartments, which provides a full compartment sealing to the unit dose in said closed lid position together with the bottom body wall, in all cartridge compartment storage positions.

In its storage position, the inhaler is desirably in a foil or aluminium pouch, or pouch or packaging of any other suitable material and under low or equilibrium humidity conditions, and the plurality of cartridge powder compartments are sealed by and between the top and bottom body walls of cylindrical or near cylindrical shape.

During use of the inhaler of the present invention, the patient removes it from its packaging and accesses the inhaler with the cartridge in the storage position. The patient then engages with the cartridge hand grip and turns and advances the first of the plurality of cartridge powder compartments into the inhalation position and, at this position, the powder compartment bottom and/or lateral air vents become aligned with the bottom and/or side openings provided in the bottom/side walls of the body opening for allowing air admission. Also, at this position, the first of the plurality of cartridge powder compartment outlet becomes aligned with the bottom inlet of the inhalation channel that is included in the top wall of the body opening.

When the cartridge has travelled into the inhalation position, the patient then inhales a first dose, according to the instructions for use, and airflow is created across the device. Air is first able travel through the body bottom and/or side air inlet and into the powder compartment through the compartment bottom and/or side inlet slit to disperse the particles there contained.

The flow of air with entrained particles then enters the body inhalation channel and the supplementary air flow provided through the body side inlets induces additional channel turbulence leading to further dispersion and deagglomeration of the particles, for entrainment and final deposition in the intended site, in the lung or in the nasal cavity, depending on the application.

Following the inhalation maneuver, the interference between the plastic protrusion included in the first and each of the plurality of powder compartments, and the plastic recess included in the body top wall prevents the mechanical return of the inhaled first cartridge powder compartment.

The patient then moves the second of the plurality of cartridge powder compartment to the inhalation position and inhales a second time, repeating the maneuver as often as there are compartments.

This novel construction allows the dispersion and deagglomeration of large dose of inhalation powders while providing an inventive assembled inhaler configuration suitable for powder filling process that minimizing drug losses, industrial complexity and manufacturing cost, while maintaining an inhaler that is simple and intuitive and maintaining the part count to two components assembled through a single and simple assembly step, and all the above features cumulative contribute to achieve a large dose inhaler manufactured at low cost, which provides an economical advantage.

Based on these advantages, it is one inventive feature of the present application that the inhaler body and cartridge are assembled prior to the powder filling into the individual cartridge compartments and the said assembled inhaler comprises an opening for filling the inhalation powder into the cartridge.

It is also an inventive feature of the present application that the assembled inhaler comprises a hinged or foldable lid made of the same material and manufactured in the same step as the inhaler body that allows the inhalation powder filling through the said opening in the inhaler assembled configuration, and the cartridge is free to advance and turn in relation to the body in said assembled inhaler configuration.

It is also an inventive feature of the present application that the assembled inhaler comprises a hinged or foldable lid made of the same material and manufactured in the same step as the inhaler body, that once moved or folded, from the open position suitable for powder filling, into the closed position, snaps into and against the inhaler body and provides close contact and interference with the cartridge and such said interference provides sealing of the filled cartridge.

It is also an inventive feature of the present invention that the assembled inhaler comprises a hinged or foldable lid made of the same material and manufactured in the same step as the inhaler body, that once moved or folded and snapped into the inhaler body, comprises the mechanism engaging with the cartridge for restraining and controlling the advancement and turning travel of the cartridge in relation to the body between multiple initial positions, where each of the plurality of cartridge compartments is sealed, into a final position where each of the plurality of cartridge compartments becomes aligned with the body inhalation channel and air inlets and outlets included in the compartment are available for air admission and in communication with the body inhalation channel, including the non-return device to provide a non-return mechanism between the cartridge and the body, once said cartridge advancement is concluded and the cartridge is locked and further movements is no longer possible.

DETAILED DESCRIPTION OF THE INVENTION

The invention will now be described on the basis of the drawings. It will be understood that the embodiments and aspects of the invention described herein are only examples and do not limit the protective scope of the claims in any way. The invention is defined by the claims and their equivalents. It will be understood that features of one aspect or embodiment of the invention can be combined with a feature of a different aspect or aspects and/or embodiments of the invention.

Referring to the drawings, numbered sequentially after the word "Fig.", like numerals indicate like parts, and each of the embodiments or aspects is identified with series of numbers where the number of hundreds is the number of the embodiment or aspect (1xx to 7xx) and the equivalent feature in each of the embodiments or aspects has the same number xx.

Figure 2A:
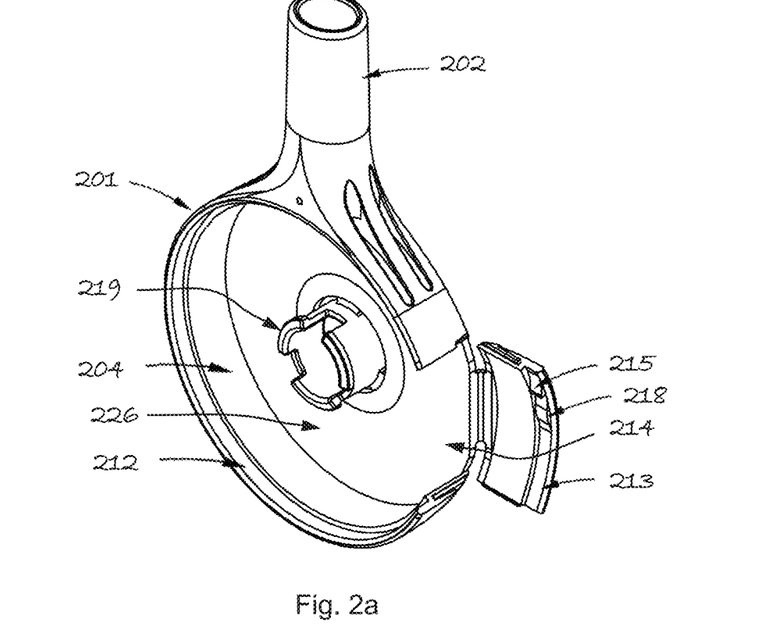
FIGS. 2a and 2b show respectively a perspective and longitudinal sectional view of an inhaler body according to the invention.
Figure 2B:
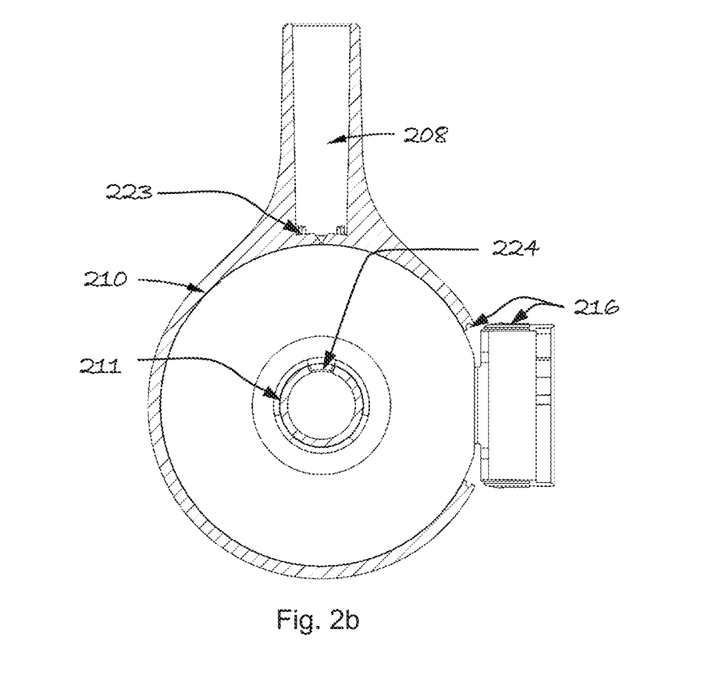

Referring to the drawings in FIGS. 2a and 2b, there is shown an inhaler body 201 comprising a mouthpiece or nosepiece 202 for engaging with the patient's mouth or nose respectively, and an opening 204 for receiving an inhaler cartridge 203, such opening 204 including top 210 and bottom 211 walls, which are of cylindrical or near-cylindrical shape and absent of any sharp edges, side walls 226, and at least one body rail 212 for allowing a turning or pivoting movement of the cartridge 203 in relation to the body 201.

FIG. 2a illustrates the inhaler body 201 which comprises a powder filling opening 214 and an hinged or foldable lid 213, included in the top wall 210 of the body opening 204, injection moulded in the same material and moulding step as the body 201 itself. FIG. 2a further shows that the hinged or foldable lid 213 further includes at least one plastic body recess 215 shaped to be engageable with corresponding cartridge protrusions 217 in the cartridge 203, to provide the device of advancing and controlling the pivoting or turning motion of the cartridge 203 in relation to the body 201, including the detent 218 to provide a non-return between the cartridge 203 and the body 201, once said advancement is concluded.

FIG. 2a additionally shows that the bottom wall 211 of the body opening 204 includes at least one plastic body protrusion 219 engageable with the corresponding bottom wall 221 of the cartridge 203, which provides a snap type assembly and the mechanical locking between the body 201 and the cartridge 203 following said assembly.

FIG. 2b further illustrates the body top wall 210 and the hinged or foldable lid 213 have a snap-type assembly 216 to provide a snap type assembly and mechanical locking of the hinged or folded lid 213 into the body top wall 210 following said assembly. In addition, there is also shown an opening 224 into the bottom wall 211 of the opening 204 shaped to receive the cartridge 203 allowing air entry into said opening 204, in alignment with a mouthpiece channel 208.

Figure 3A:
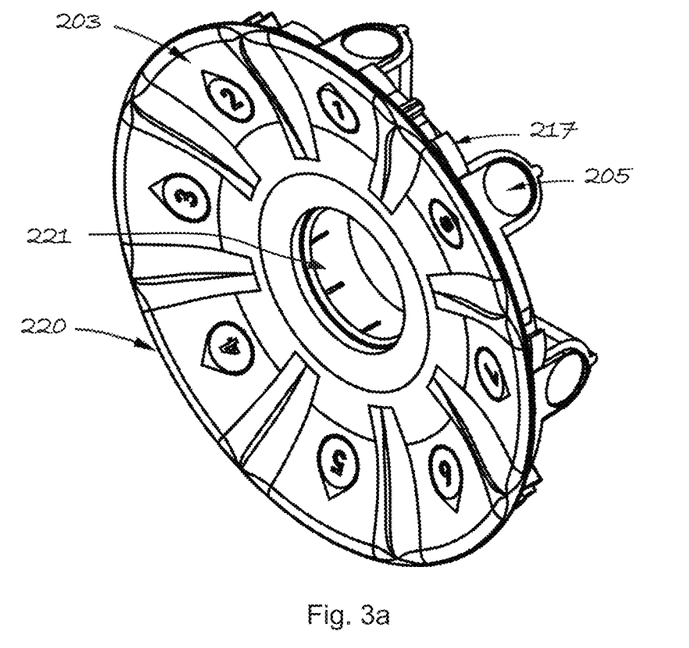
FIGS. 3a and 3b show respectively a perspective and transversal sectional view of an inhaler cartridge according to the invention.
Figure 3B:
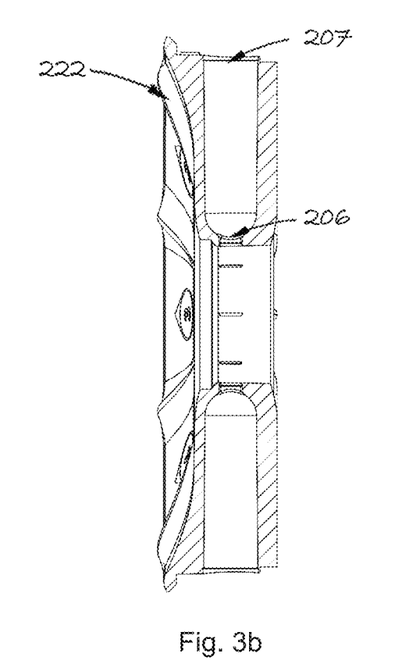

Referring to the drawings in FIGS. 3a and 3b, there is shown the inhaler cartridge 203 comprising cylindrical or near-cylindrical cartridge top 220 and cartridge bottom 221 walls, absent of sharp edges, and a plurality of powder compartments 205, each with an inlet 206 and outlet 207, which is suitable for filling, storing and delivery inhaled powder formulations.

FIG. 3a further illustrates the inhaler cartridge 203 comprises at least one plastic cartridge protrusion 217 at the cartridge top wall 220 for each of the plurality of powder compartments 205, which are engageable with the corresponding body hinged lid plastic body recess 215 and the detent 218, to provide the device for advancing and controlling the pivoting or turning motion of the cartridge 203 within the body rail 212 in relation to the inhaler body 201, between multiple positions, including the non-return device to provide a non-return once said advancement is concluded.

FIG. 3b additionally illustrates that the inhaler cartridge 203 includes at least one hand grip 222 engageable with the patient's fingers to provide a turning device for turning the cartridge 203 in relation to the body 201 between multiple positions.

Figures 4A, 4B:
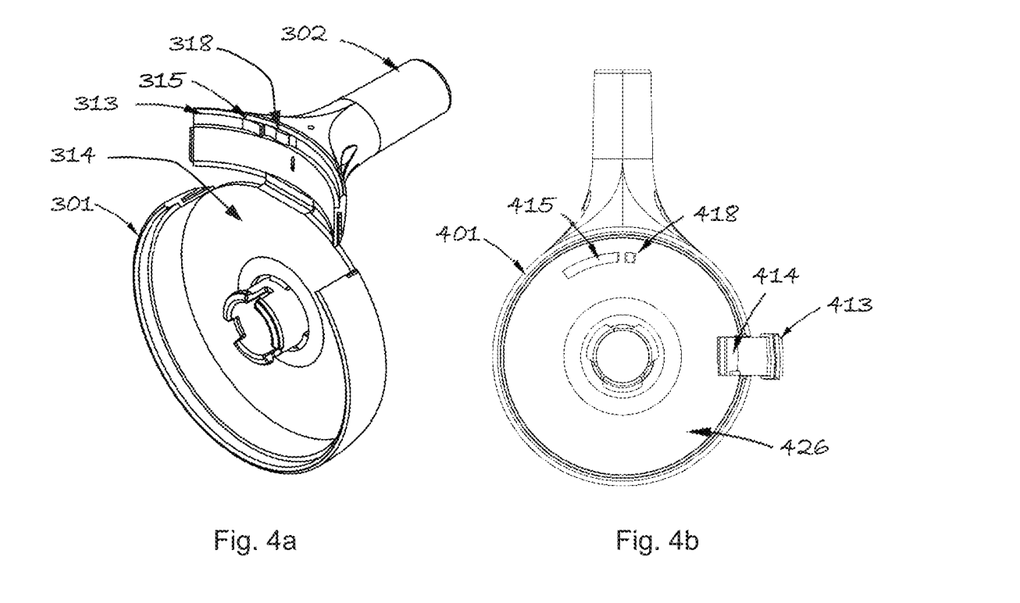
FIGS. 4a and 4b show respectively perspective and frontal views of additional aspects of an inhaler body according to the invention.

Referring to FIG. 4a, there is shown a second aspect of the inhaler body 301 where an hinged or foldable lid 313 with a plastic body recess 315 and a detent 318 form a device for controlling the advancement of the inhaler cartridge 203 and are integrated with the mouthpiece or nosepiece 302.

FIG. 4b shows a third aspect of the inhaler body 401 where a plastic body recess 415 and a detent 418 form the device for controlling the advancement of the cartridge and are integrated into the inhaler body side walls 426.

Figure 5A:
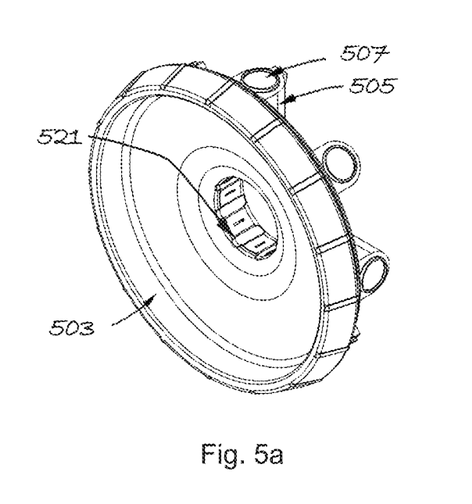
FIGS. 5a and 5b show perspective views of additional aspects of an inhaler cartridge according to the invention.
Figure 5B:
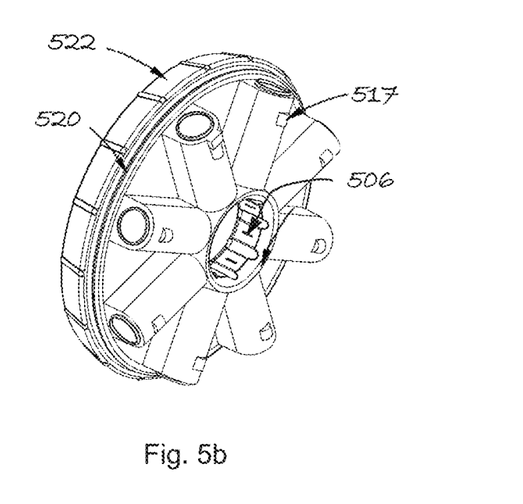

FIGS. 5a and 5b show a second aspect of the inhaler cartridge 503 where the cartridge protrusions 517 are located in the frontal wall of each of the powder compartments 505, engageable with the corresponding body protrusions (i.e. the plastic body recess 415 and the detent 418) of the third aspect of the inhaler body 401 shown in FIG. 4b, to provide the device for advancing and controlling the pivoting or turning motion of the cartridge 503 in relation to the body 401, between the multiple positions, by means of the actuation of the hand grip 522 by the patient's fingers.

Figure 6A:
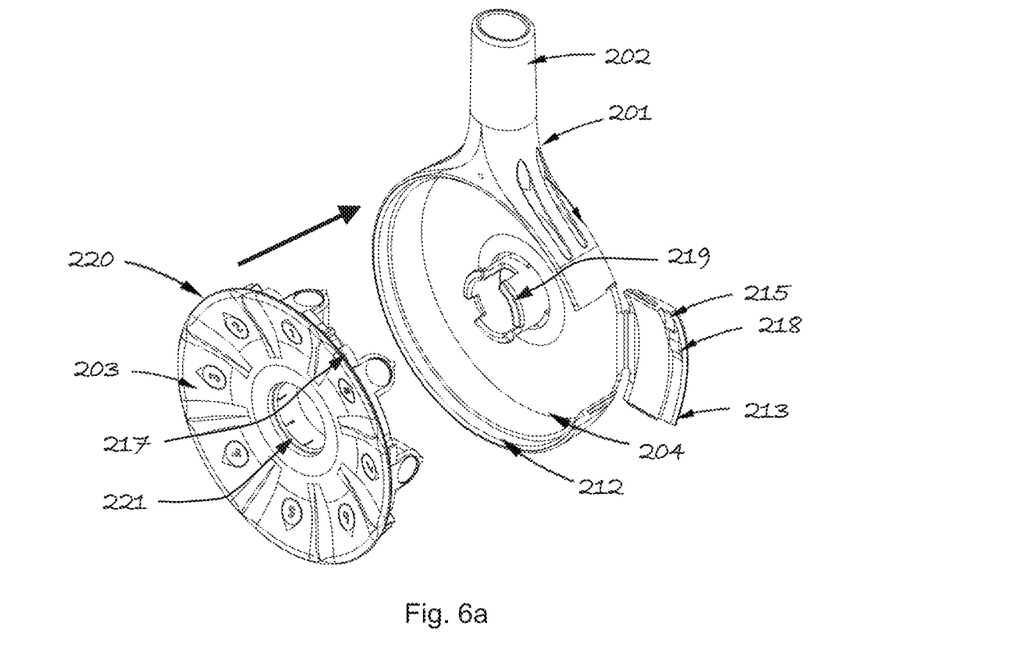
FIG. 6a shows a perspective view of an inhaler body according to FIG. 2 and an inhaler cartridge according to FIG. 3 in the disassembled configuration.
Figure 6B:
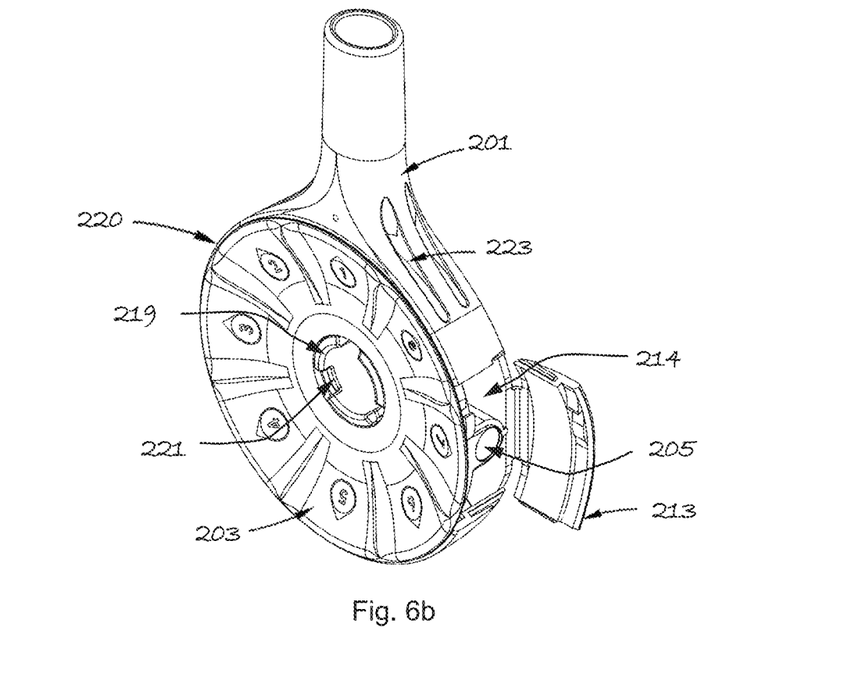
FIG. 6b shows a perspective view of an inhaler body according to FIG. 2 and an inhaler cartridge according to FIG. 3 following the assembly step, in the assembled configuration, with the hinged lid in the open position, making the device available for powder filling.

Referring next to FIG. 6, there is shown the assembly of the inhaler comprised by the inhaler body 201 and the inhaler cartridge 203. FIG. 6a illustrates that, following manufacturing, the inhaler cartridge 203 is inserted into the inhaler body 201 through the opening 204. FIG. 6b shows that the snap type engagement between the plastic body protrusions 219 and the cartridge bottom wall 221 provides full mechanical locking between the inhaler body 201 and the inhaler cartridge 203 following the assembly step, while the engagement of the cartridge top wall 220 with the body rail 212 allows for free turning movement between the inhaler cartridge 203 and the inhaler body 201.

FIG. 6b further illustrates that, following assembly, each of the powder compartments 205 is available for filling with a powder unit dose through the body powder filling opening 214, since the body hinged or foldable lid 213 is in the opening position from the injection moulding process of the inhaler body 201, and the inhaler cartridge 203 is free to turn sequentially in relation to the inhaler body 201, without mechanical constraints.

Figure 7A:
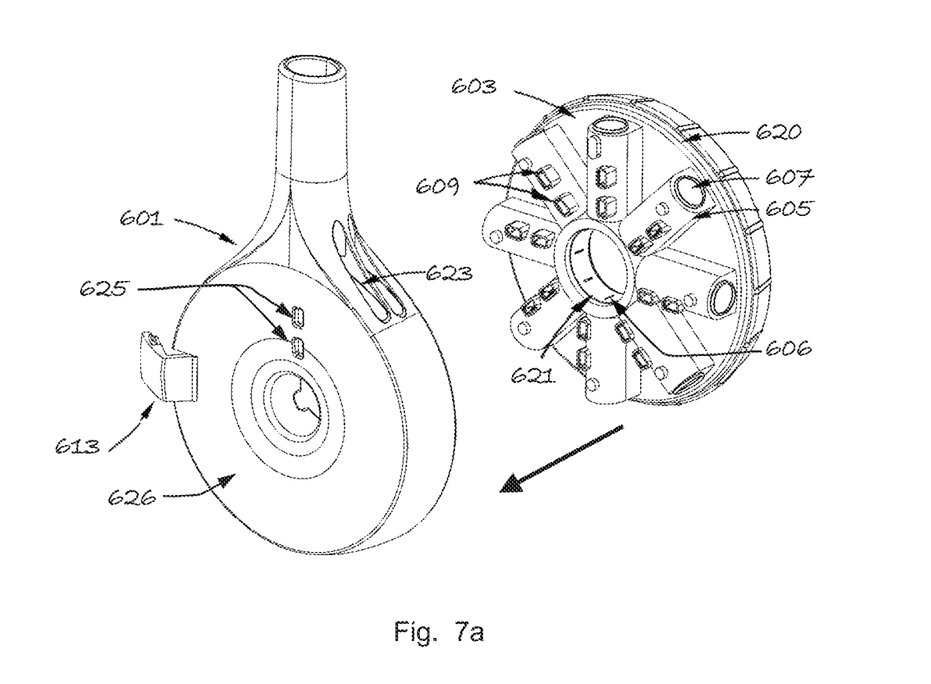
FIGS. 7a and 7b show perspective views of another aspect of an inhaler body and an inhaler cartridge according to the invention respectively in the disassembled and assembled configurations.
Figure 7B:
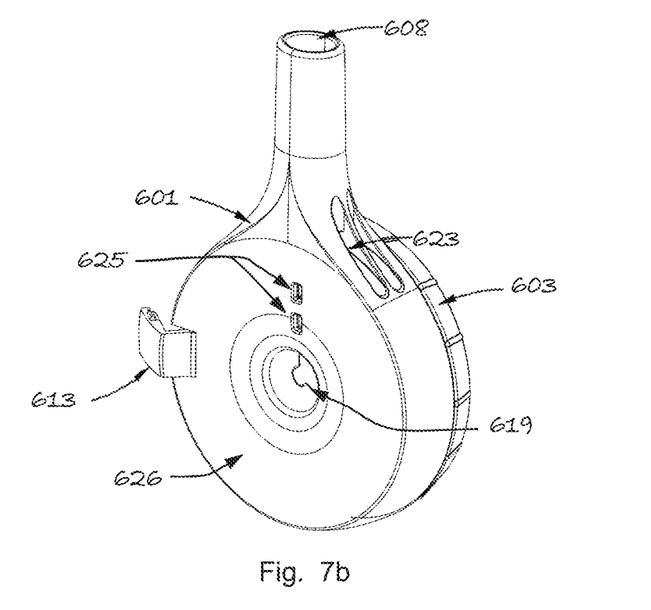

FIG. 7a additionally shows the assembly of a second inhaler aspect comprised by the inhaler body 601 and the inhaler cartridge 603, where side air inlets 609 are included in each of the powder compartments 605 for additional, tangential air admission into the powder compartments 605 leading to the generation of the effective dispersive and aerosolization dynamics disclosed in the afore-mentioned Portuguese patent application PT103481. FIG. 7b illustrates that, following assembly, the side air inlets 625 comprised in the inhaler body side walls 626 allow for air admission into each of the powder compartments 605 through the compartment side air inlets 609, when said powder compartment 605 reaches the inhalation position aligned with the mouthpiece channel 608.

Referring next to FIG. 8, there is shown the filling of an inhaler. FIG. 8a illustrates the powder filling of a unit dose by conventional equipment into the first cartridge powder compartment 705 through the body powder filling opening 714 while the body lid 713 is in the opened position. FIG. 8b shows the turning of the inhaler cartridge 703 until the second powder compartment 705 is aligned with the body powder filling opening 714 and is available and ready to be filled. FIG. 8c then illustrates the powder filling of a second unit dose by conventional equipment into the second cartridge powder compartment 705 through the powder filling opening 714 while the body hinged lid 713 is in the open position.

Figure 8A:
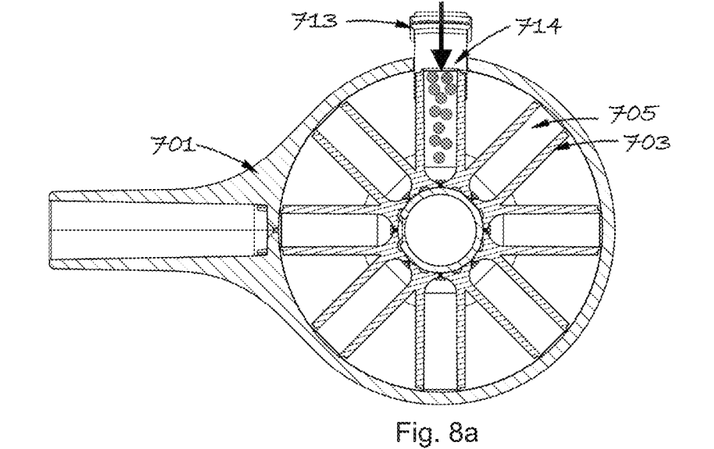
FIGS. 8a to 8c show longitudinal sectional views of an inhaler according to the invention during powder filling into the plurality of powder compartments.
Figure 8B:
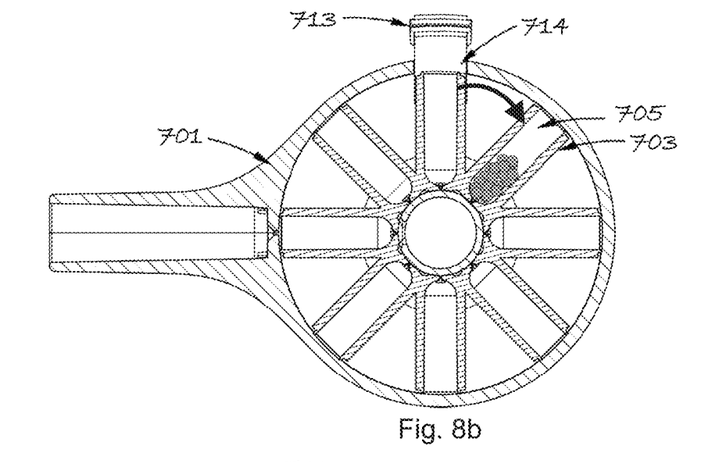
Figure 8C:
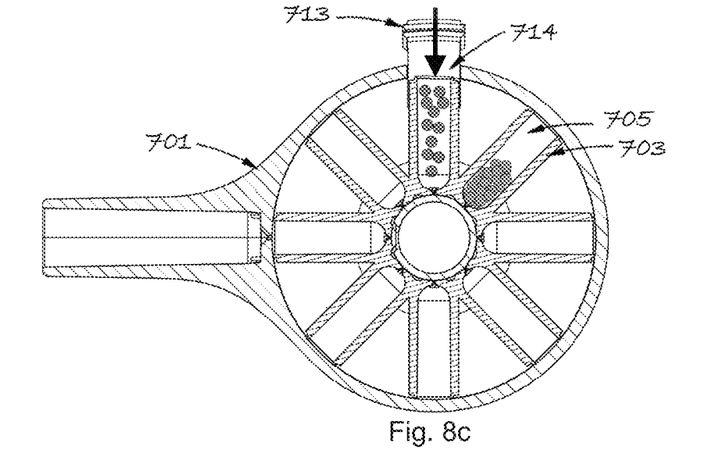
Figure 8D:
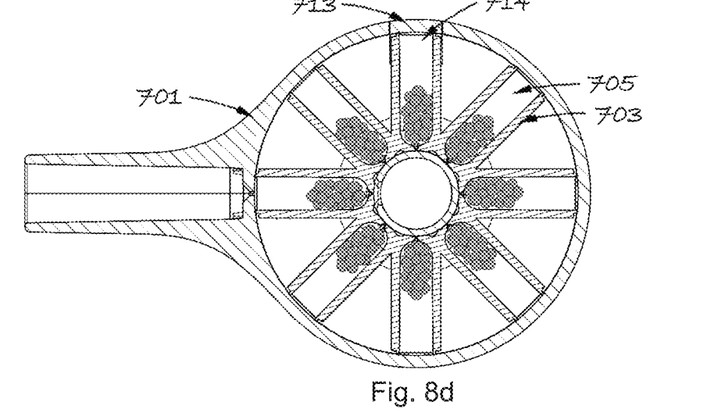
FIGS. 8d to 8f show longitudinal sectional views of an inhaler according to the invention following powder filling into the plurality of powder compartments, when the hinged lid has been moved into the closed position.
Figure 8E:
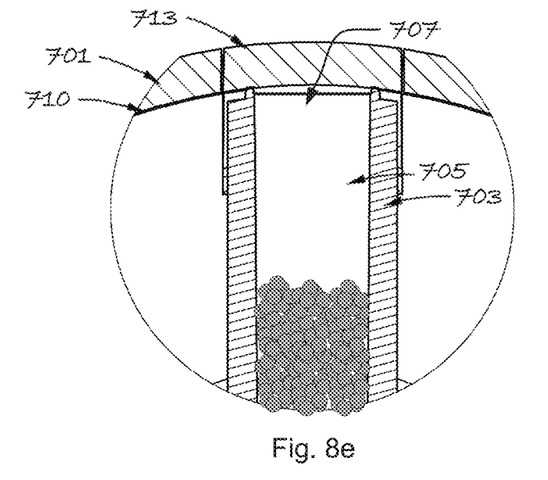
Figure 8F:
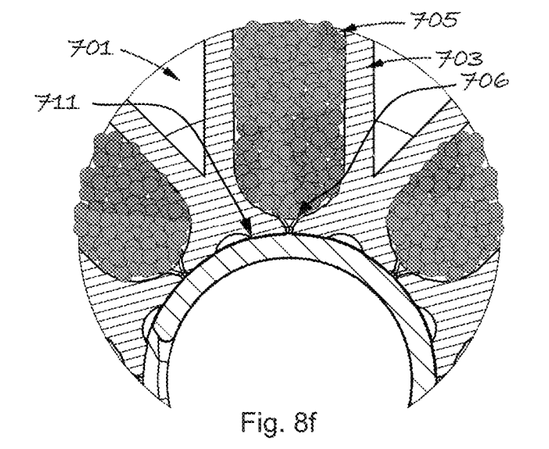

FIGS. 8d to 8f show that, following filling of a unit dose into the last available cartridge powder compartment 705, the body lid 713 is moved or folded from the open position into the closed position and snapped into and against the body top wall 710 of the inhaler body 701, providing close mechanical contact and sealing interference with the outlet 707 of each of the cartridge powder compartments 705 and, together with the close contact and sealing interference of the body bottom wall 711 with the cartridge powder compartment bottom inlet 706, providing the full powder compartment 705 sealing to the powder unit dose, across all cartridge compartment storage positions.

Figure 9:
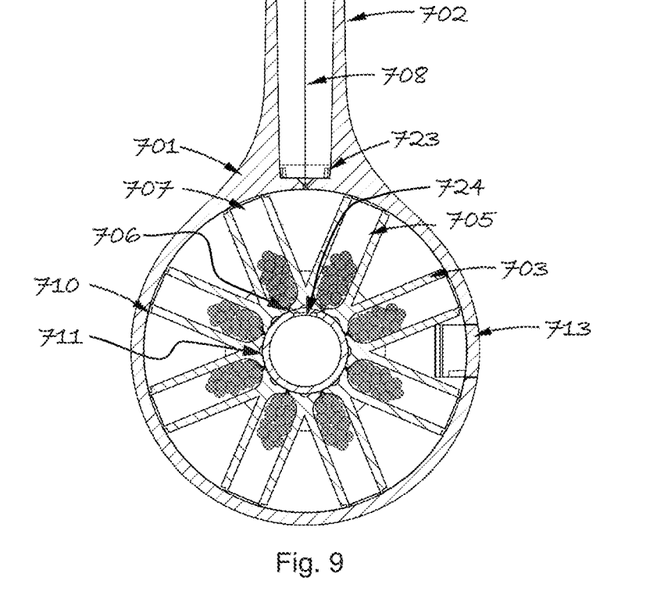
FIG. 9 shows a longitudinal sectional view of an inhaler according to FIG. 8, following powder filling and closing of the hinged lid, when the inhaler cartridge is in the storage position.

FIG. 9 illustrates the inhaler when the patient removes the inhaler from the packaging and accesses the inhaler with the inhaler cartridge 705 in the storage position, where each of the plurality of the powder compartments 705 is sealed by the body bottom wall 711, the body top wall 710 and the closed body lid 713.

Figure 10:
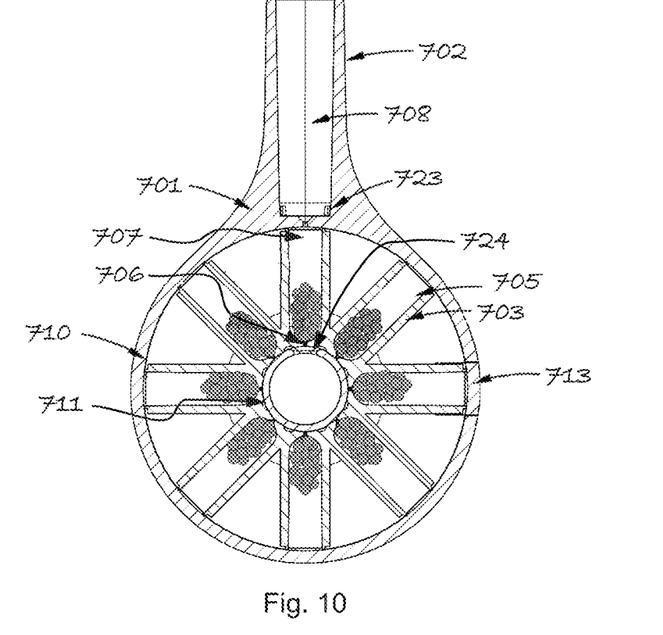
FIG. 10 shows a longitudinal sectional view of the inhaler according to FIG. 8, following powder filling and closing of the hinged lid, when the inhaler cartridge has been moved from the storage position into the inhalation position.

Referring next to FIG. 10, there is shown an inhaler when the patient engages with the cartridge hand grip 522 and turns to advance the first of the powder compartments 705 into the inhalation position. At this position, cartridge powder compartment bottom inlet 706 becomes aligned with the bottom wall opening 724, thus allowing air admission into the powder compartment 705, and the cartridge powder compartment outlet 707 becomes aligned with the mouthpiece channel 708, thus allowing fluid communication with the patient's airways and dispersion of the powder unit dose included in said powder compartment 705 through the patient's inspiratory effort.

Figure 11:
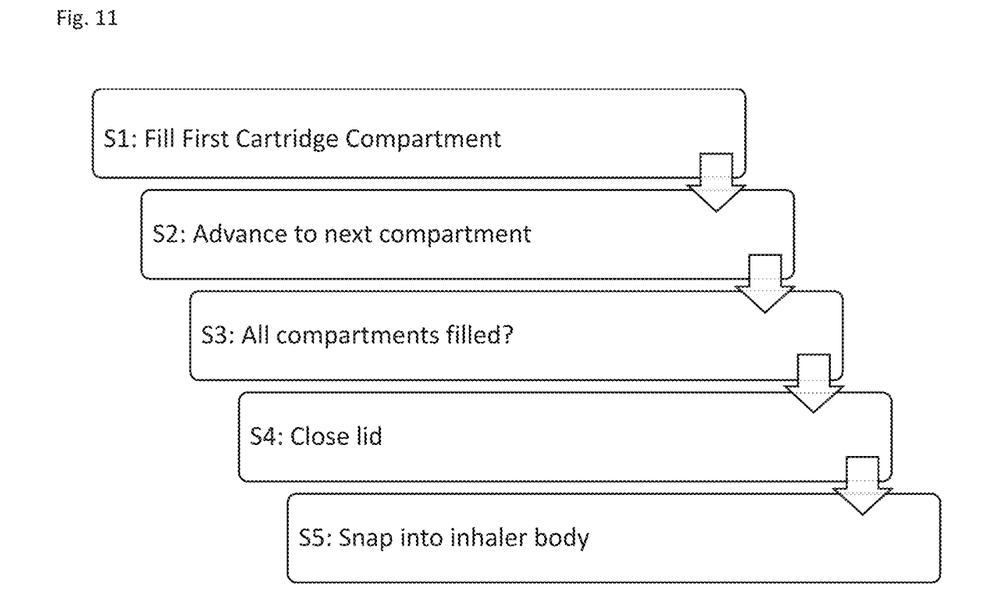
FIG. 11 shows an outline of the filling method.

FIG. 11 shows the outline of the method to fill the dry powder inhaler. In a first step S1, a first one of the drug doses are filled in the assembled inhaler through a filling opening 214; 314; 414; 71 in the body 213; 313; 413; 613; 713 into a first one of the individual cartridge compartments 205; 505; 605; 705. In step S2 the cartridge compartment 205; 505; 605; 705 is advanced to the next drug compartment filling position until in step S3 all of the cartridge compartments 205; 505; 605; 705 are filled. In step S4, the hinged or foldable body lid 213; 313; 413; 613; 713 is closed and the snapped in step S5 into and against the inhaler body (213; 313; 413; 613; 713).

The invention claimed is:

1. A dry powder inhaler suitable for pulmonary or nasal delivery, comprising an inhaler body and a cartridge the inhaler comprising:
   a. the inhaler body comprising a mouthpiece; an inhalation channel for providing fluid communication between the patient's mouth when engaged with the mouthpiece; a bottom channel inlet; side inlets for allowing direct air admission from atmosphere into the inhalation channel; an inhaler body opening formed in the inhaler body and defined between opposing top and bottom walls and opposing side walls, said inhaler body opening having at least one end open by means of which the cartridge may be mounted into the inhaler body opening; one or more plastic body protrusions for engaging and locking the cartridge once mounted in said inhaler body opening; one or more body rails in the said inhaler body opening shaped for receiving the cartridge and one or more body recesses and detents commonly adapted for movement of the cartridge relative to the body; and
   b. the cartridge comprising a plurality of powder compartments of tapered cylindrical or cylindrical shape formed therein for carrying a powder-based medicament; bottom walls that engage with the plastic body protrusions for engaging and locking the cartridge once mounted in said inhaler body opening; top walls that engage with the body rails; one or more cartridge protrusions that engage with the one or more plastic body recesses and detents provided in the body for allowing the movement of the cartridge in relation to the body from a storage position into an inhalation position, when the cartridge is mounted in the inhaler body opening shaped for receiving the cartridge; and a bottom inlet slit and top outlet hole;

c. the plurality of powder compartments are configured to turn and advance in sequence inside the body from the storage position where there is no fluid air communication into the plurality of powder compartments, into the inhalation position, where there is sequential alignment and fluid air communication between the body bottom or the side inlets, each of the plurality of cartridge powder compartment bottom or side inlet slits, the cartridge top outlet and the mouthpiece channel;

wherein the inhaler body and cartridge are assembled prior to powder filling into individual cartridge compartments and the said assembled inhaler comprises a body filling opening for filling the inhalation powder into the cartridge, and wherein the bottom channel inlet or the side inlets are arranged to enable air admission through one of the plurality of powder compartments and thus allowing dispersion of the inhalation powder; wherein the assembled inhaler comprises a hinged or foldable lid in the inhaler body that allows the powder filling of the inhalation powder through the said body filling opening in the inhaler assembled configuration.

2. The dry powder inhaler of claim 1, wherein the cartridge is configured, during powder filling, to advance and turn unrestrained in relation to the body in said assembled inhaler configuration for filling a unit dose of the inhalation powder into each of the plurality of cartridge compartments.

3. The dry powder inhaler of claim 1, wherein each of the plurality of cartridge compartments is configured, during powder filling, to be sealed by close contact with the bottom walls in the body opening shaped for receiving the cartridge.

4. The dry powder inhaler of claim 1, wherein the body hinged or foldable lid, once the last unit dose of powder has been filled into the plurality of cartridge compartments, is moved and snapped into and against the body, providing mechanical interference with the cartridge outlet and such said mechanical interference closes the inhaler body filling opening and provides sealing of the filled cartridge.

5. The dry powder inhaler of claim 1, wherein the body hinged or foldable lid, once moved or folded and snapped into and against the body, comprises at least one plastic body recess and detent engaging with at least one compartment protrusion comprised in each of the plurality of cartridge compartments for restraining and controlling the sequential advancement and turning travel of the cartridge in relation to the body between multiple initial positions, at which multiple positions each of the plurality of cartridge compartments is sealed, into a final position at which final position each of the plurality of cartridge compartments becomes aligned with the body inhalation channel, and the air inlets and the outlets included in the compartment are available for air admission and in communication with the body inhalation channel.

6. The dry powder inhaler of claim 1, wherein the body hinged or foldable lid, once moved and snapped into and against the body, comprises a detent between the cartridge and the body, once each cartridge movement is concluded.

7. The dry powder inhaler of claim 1, wherein the inhaler cartridge comprises at least one cartridge hand grip or holder, adapted for turning or advancing the cartridge in relation to the body.

8. A method to fill a dry powder inhaler, the inhaler comprising:

a. an inhaler body comprising one or more body recesses and detents adapted for movement of the cartridge relative to the body; and b. a cartridge mounted in the inhaler body and comprising a plurality of powder compartments of tapered cylindrical or near-cylindrical shape formed therein for carrying a powder-based medicament; one or more cartridge protrusions that engage with the one or more plastic body recesses and detents provided in the body for allowing the movement of the cartridge in relation to the body from a storage position into an inhalation position;

c. the cartridge further comprising a plurality of powder compartments turning and advancing in sequence inside the body from a storage position where there is no fluid air communication into the plurality of powder compartments, into an inhalation position where there is fluid air communication into the plurality of powder compartments;

wherein the method comprises filling plurality of drug doses are filled in the assembled inhaler, through a filling opening in the inhaler body, into each individual cartridge compartment, the cartridge compartment being advanced to the next drug compartment filling position until all cartridge compartments are filled and the hinged or foldable body lid is closed and snapped into and against the inhaler body.

* * * * *